US011355330B2

(12) United States Patent
Meissner et al.

(10) Patent No.: US 11,355,330 B2
(45) Date of Patent: Jun. 7, 2022

(54) USES OF ISOBARIC TAGS IN MASS SPECTROMETRY

(71) Applicant: Max-Planck-Gesellschaft zur Förderung der Wissenschaften e.V., Munich (DE)

(72) Inventors: Felix Meissner, Berlin (DE); Matthias Mann, Munich (DE); Florian Meier, Pullach (DE); Sebastian Virreira Winter, Munich (DE); Arturo Zychlinsky, Berlin (DE)

(73) Assignee: MAX-PLANCK-GESELLSCHAFT ZUR FÖRDERUNG DER WISSENSCHAF 1 EN E.V., Munich (DE)

( * ) Notice: Subject to any disclaimer, the term of this patent is extended or adjusted under 35 U.S.C. 154(b) by 0 days.

(21) Appl. No.: 16/763,968

(22) PCT Filed: Nov. 14, 2018

(86) PCT No.: PCT/EP2018/081243
§ 371 (c)(1),
(2) Date: May 13, 2020

(87) PCT Pub. No.: WO2019/096852
PCT Pub. Date: May 23, 2019

(65) Prior Publication Data
US 2020/0286721 A1     Sep. 10, 2020

(30) Foreign Application Priority Data
May 17, 2018    (EP) .................................... 18173036

(51) Int. Cl.
    *H01J 49/00*      (2006.01)
    *C07D 207/40*      (2006.01)
    *G01N 33/68*      (2006.01)

(52) U.S. Cl.
    CPC .......... *H01J 49/004* (2013.01); *C07D 207/40* (2013.01); *G01N 33/6848* (2013.01); *H01J 49/0036* (2013.01)

(58) Field of Classification Search
    CPC ...... H01J 37/295; H01J 37/20; H01J 49/4215; H01J 37/26; H01J 2237/05;
    (Continued)

(56) References Cited

U.S. PATENT DOCUMENTS 7,195,751 B2 * 3/2007 Pappin ................. C07D 401/12
                                                                                                424/1.81
8,309,359 B2 * 11/2012 Sohn .................... C07D 249/04
                                                                                                436/56

(Continued)

FOREIGN PATENT DOCUMENTS

WO     2004/070352 A2     8/2004
WO     2018/087397 A2     5/2018

OTHER PUBLICATIONS

Patent Cooperation Treaty, International Search Report and Written Opinion issued in PCT/EP2018/081243, dated Mar. 11, 2019, pp. 1-25.

(Continued)

*Primary Examiner* — David A Vanore
(74) *Attorney, Agent, or Firm* — Pillsbury Winthrop Shaw Pittman LLP (57) ABSTRACT

The present invention relates to use of an isobaric label in mass spectrometry (MS) analysis using data-independent acquisition (DIA), wherein said isobaric label comprises or consists of a group which fragments in the mass spectrometer (i) at an energy below the energy required for fragmenting analyte-derived precursor ions and/or a higher conversion rate than said precursor ions; and (ii) at said energy according to (i) and when coupled to a precursor ion, at a single site within said group, to yield a first moiety and a (Continued)

second moiety, said second moiety being coupled to said precursor ion.

8 Claims, 2 Drawing Sheets

(58) Field of Classification Search
 CPC .............. H01J 2237/2614; H01J 49/004; H01J 49/0036; G01N 1/34; G01N 1/28; G01N 27/62; G01N 35/10; G01N 33/6848; C07D 207/40
 See application file for complete search history.

(56) References Cited

U.S. PATENT DOCUMENTS

| | | | | |
|---|---|---|---|---|
| 10,978,272 B2* | 4/2021 | Vystavel | ............... | H01J 37/304 |
| 2003/0052266 A1* | 3/2003 | Shimomura | .......... | H01J 49/147 250/281 |
| 2008/0250881 A1* | 10/2008 | Dona | ...................... | H01J 37/20 73/864.91 |
| 2014/0065319 A1* | 3/2014 | Randolph | ............... | C23C 16/18 427/551 |
| 2015/0241437 A1* | 8/2015 | Zhang | .................... | G01N 33/58 506/12 |
| 2017/0082635 A1 | 3/2017 | Rychnovsky | | |
| 2018/0238792 A1* | 8/2018 | Miyamoto | ........... | G01N 23/225 |
| 2018/0299464 A1* | 10/2018 | Li | ....................... | G01N 33/6812 |
| 2019/0206664 A1* | 7/2019 | De Marco | ......... | H01J 37/32009 |
| 2020/0199071 A1* | 6/2020 | Carell | ................... | C07C 317/50 |
| 2020/0411282 A1* | 12/2020 | Straw | ...................... | H01J 37/20 |

OTHER PUBLICATIONS

Rauniyar et al., "Isobaric Labeling-Based Relative Quantification in Shotgun Proteomics", Journal of Proteome Research, Nov. 4, 2014, pp. 5293-5309, vol. 13(12).

Silveira et al., "Parallel accumulation for 100% duty cycle trapped ion mobility-mass spectrometry", International Journal of Mass Spectrometry, Mar. 14, 2016, pp. 168-175, vol. 413.

Anonymous, "Thermo Scientific Orbitrap Elite High-Field Orbitrap Hybrid Mass Spectrometer", Jan. 1, 2016, pp. 1-4, Retrieved from Internet URL:https://assets.thermofisher.com/TFS-Assets/CMD/Specification-Sheets/PS-30229-MSOrbitrap-Elite-PS30229-EN.pdf, retrieved on Nov. 13, 2018.

Chapman et al., "Multiplexed and data-independent tandem mass spectrometry for global proteome profiling", Mass Spectrometry Reviews, Nov. 26, 2013, pp. 452-470, vol. 33(6).

Virreira Winter, et al. "EASI-tag enables accurate multiplexed and interference-free MS2-based proteome quantification", Nature Methods, Jun. 18, 2018, pp. 527-530, vol. 15(7).

* cited by examiner

Figure 1

Figure 2 a) Standard DIA b) DIA with isobaric labels using low molecular weight reporters c) DIA with isobaric labels using peptide-coupled reporter ions (new invention)

USES OF ISOBARIC TAGS IN MASS SPECTROMETRY

RELATED APPLICATIONS

This patent application is the National Phase of International Application No. PCT/EP2018/081243, filed Nov. 14, 2018, which designated the U.S. and that International Application was published under PCT Article 21(2) in English, which claims the benefit of priority to European Patent Application No. 18173036.7, filed May 17, 2018, and which claims the benefit of priority to International Application No. PCT/EP2017/079211, filed 15 Nov. 14, 2017. The entire contents of the foregoing applications are incorporated herein by reference, including all text, tables and drawings.

SUMMARY

The present invention relates to use of an isobaric label in mass spectrometry (MS) analysis using data-independent acquisition (DIA), wherein said isobaric label comprises or consists of a group which fragments in the mass spectrometer (i) at an energy below the energy required for fragmenting analyte-derived precursor ions and/or a higher conversion rate than said precursor ions; and (ii) at said energy according to (i) and when coupled to a precursor ion, at a single site within said group, to yield a first moiety and a second moiety, said second moiety being coupled to said precursor ion.

DETAILED DESCRIPTION

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Analysis by mass spectrometry (MS) in the field of complex mixtures such as in the study of biological systems is constantly expanding. Mass spectrometry can be used to determine the identity of analytes as well as their quantities. Experience tells that analysis in the detector, for example an Orbitrap detector, is the rate-limiting step. For the purpose of increasing throughput, procedures have been developed which involve the pooling of samples after analytes in each sample have been differentially labeled. This is known in the art as isobaric labeling. Established forms of isobaric labeling are known as TMT and iTRAQ. Isobaric labels are conjugated to analytes, typically peptides, and subsequently fragmented in the mass spectrometer. When using art-established isobaric labels, it is not possible to fragment only the label, but not the peptide analyte. When the analyte-label conjugate fragments, at least one fragment is formed which comprises a part of the peptide analyte. At least a further fragment is formed which does not comprise any part of the peptide analyte. Only the latter can be used for quantitation when relying on art-established isobaric labels. This has important consequences for the mode of operation of the mass spectrometer. Since the fragment used for quantitation contains no information about the peptide-label conjugate it is derived from, quantitation is only possible when a very limited m/z range (essentially corresponding to a single analyte) is isolated and analyzed. This has severe implications for throughput and/or spectral resolution, especially in a setting where the mass spectrometer is coupled online to a device providing constant sample output such as a liquid chromatography device.

In view of the above, a better utilization of time on the mass spectrometer is highly desirable. Such better utilization may be achieved by better time management of the mass spectrometer as such on the one hand, and by the use of advanced isobaric labels on the other hand. The present invention addresses the prior art deficiencies via both routes which may be used independently or in combination.

Accordingly, in a first aspect the present invention relates to use of an isobaric label in mass spectrometry (MS) analysis using data-independent acquisition (DIA), wherein said isobaric label comprises or consists of a group which fragments in the mass spectrometer (i) at an energy below the energy required for fragmenting analyte-derived precursor ions and/or a higher conversion rate than said precursor ions; and (ii) at said energy according to (i) and when coupled to a precursor ion, at a single site within said group, to yield a first moiety and a second moiety, said second moiety being coupled to said precursor ion.

The term "data-independent acquisition", abbreviated "DIA", in conjunction with MS has its art-established meaning (Gillet et al. 2012, doi: 10.1074/mcp.O111.016717). Typically, it refers to the analysis in an MS2 scan of m/z ranges having breadths which generally comprise multiple analytes. Number or type of peaks in the MS1 scan are typically of no influence on the choice of the m/z range; see also further below.

It is understood that the term "precursor ion" does not designate a single ion or single molecule, but instead a plurality of molecules or ions of the same species, i.e. of the same chemical composition and constitution.

Furthermore, it is understood that the term "isobaric label", e.g. when used in conjunction with a plurality of samples, refers in fact to a set of labels. These labels in such a set are chemically identical, but have different isotope substitution patterns. This is further explained and illustrated in the following section entitled "isobaric labels".

Preferred analytes are peptides. As known in the art, peptides are obtained by proteolytic, preferably tryptic digestion of polypeptides or proteins.

Isobaric Labels

Isobaric labels in accordance with the first aspect have been disclosed in the earlier international patent application WO 2018/087397. The entire disclosure content of this earlier application is part of the present invention and hereby incorporated by reference. We note that the above recited "group which fragments in the mass spectrometer" has its counterpart in a "moiety which fragments in the mass spectrometer" in WO 2018/087397.

It is furthermore understood that isobaric labels, prior to being conjugated to an analyte, contain a reactive group. This reactive group is also designated "reactive moiety" in WO 2018/087397.

The term "isobaric label" is used, depending on the context, to designate one of two possibilities: first, a compound comprising a moiety capable of fragmenting and a reactive moiety—this is the isobaric label prior to conjugating it to any analyte; and secondly the isobaric label in its form conjugated to an analyte in which case the reactive moiety is no longer present.

With regard to isobaric labels which comprise a reactive moiety, and relying on the disclosure of WO 2018/087397, an isobaric label is a compound which comprises or consists of (a) a reactive moiety, said reactive moiety being capable of reacting with a functional group of a peptide to form a covalent bond; and covalently joined thereto (b) a moiety which fragments in the mass spectrometer (i) at an energy below the energy required for fragmenting peptides and/or a higher conversion rate than peptides; and (ii) at said energy according to (i) and when coupled to a peptide via said reactive group, at a single site within said compound coupled to a peptide, to yield a first moiety and a second moiety, said second moiety being coupled to said peptide.

This compound is designed for being covalently joined to a peptide, polypeptide or protein. This is implemented by requirement (a). A number of chemistries for coupling a compound to a peptide are available and known to the skilled person. Preferred and/or exemplary solutions to that end will be disclosed in further detail below. A preferred functional group of a peptide, polypeptide or protein which is capable of reacting with a reactive moiety in accordance with the first aspect is an amino group, for example the N-terminal main chain amino group of a peptide, polypeptide or protein or a side chain amino group. Accordingly, a preferred reactive moiety is an amine-reactive moiety.

Upon reacting with an analyte, more specifically a peptide, a compound-peptide conjugate is formed. Upon fragmentation at said single site, said compound-peptide conjugate yields said first moiety and a second conjugate. The second conjugate is a conjugate of said peptide with the remaining part of said compound of the invention (second moiety) after loss of said first moiety. If a plurality of peptides is derivatized with the same, fragmentation will yield a plurality of second conjugates. These second conjugates have a constant and a variable part. The variable part is determined by the specific peptide comprised in a specific second moiety, and the constant part is that component of the second conjugate which originates from said compound. This part is herein also referred to as constant part of the second conjugate. In the art, and in relation to isobaric tags which are distinct from the isobaric tags disclosed here, the constant part is also referred to as "balancing moiety". The second moiety or constant part is constant in the sense that it has always the same chemical structure for a given compound. As regards isotopic substitution, it is understood that within a set of compounds having the same structure, said second moieties or constant parts differ from each other with regard their isotopic substitution, the consequence being that different second moieties within such set of compounds have different masses, at least different exact masses and preferably also different nominal masses. In terms of structure, the second moiety constant part is generally that part of a compound which begins with the cleavable bond and ends with the atom preceding the first atom of the analyte or peptide in said second conjugate. Under certain circumstances, a loss of a proton, hydrogen or water or the like may occur.

Covalently joined to said reactive moiety, said compound furthermore comprises or additionally consists of a moiety which fragments in the mass spectrometer. An important feature in that respect is that fragmenting occurs at an energy which is below the energy required for fragmenting analytes, in particular peptides. Alternatively or in addition, the moiety fragments in the mass spectrometer with a higher conversation rate than analytes, in particular peptides. The term "conversion rate" is defined further below. Generally speaking, the requirement of a higher conversion rate than peptides applies to all energies below full peptide fragmentation. In a preferred embodiment, peptide fragmentation occurs at normalized high energy collisional dissociation (HCD) collision energies (NCE) of above about 30, for example in the interval between about 23 and about 30. The moiety (b) in accordance with the present invention preferably fragments at normalized HCD collision energies (NCE) below about 23.

While fragmentation thresholds are defined by reference to HCD collision energies, uses of compounds of the invention are not limited to a particular dissociation method. E.g., collision-induced dissociation (CID), SID, ETD, ECD orphotodissociation may be used as well.

It is established in the art that the mass spectrometer can be operated in different modes. Modes can be distinguished by the energy acquired by the ions in the mass spectrometer. In relation to analytes which are peptides, polypeptides or proteins, a mass spectrometer can be operated in a fragmenting mode and a non-fragmenting mode. While in the non-fragmenting mode the analytes are essentially left intact, this does not apply to the fragmenting mode. Owing to the use of higher energies, analytes, especially peptides, polypeptides and proteins will fragment. A mass spectrometer may also be operated such that it rapidly switches between the two modes such that a given fraction or sample is analyzed concomitantly in a fragmenting and a non-fragmenting mode.

While the prior art provides isobaric labels which fragment at an energy where also peptides fragment, this does not apply to the mentioned compounds or isobaric labels. Moiety (b) fragments at lower energies and/or with a higher conversion rate. As a consequence, the compound offers an option to operate the mass spectrometer at an energy where only moiety (b) fragments, but peptides do not fragment, and/or to operate it such that the moiety (b) fragments with a higher conversion rate than peptides. In accordance with the latter functional requirement it is understood that peptide fragmentation at a given energy does not have to be completely absent. Instead, what matters is that moiety (b) fragments with a higher conversion rate at a given energy. Thresholds are defined further below. Obviously, at sufficiently high energies, both moiety (b) and peptides will fragment to comparable and high degrees.

In a preferred embodiment, the above mentioned fragmenting of peptides is fragmenting of the peptide backbone. The term "peptide backbone" has its art-established meaning. It refers to the covalent chain formed by the nitrogen atom of the alpha amino group, the alpha carbon atom and the carbon atom of the carbonyl group directly bound to the alpha carbon atom of each constituent amino acid of a given peptide.

The term "higher conversion rate" preferably refers to at least 2-fold more fragmented moiety (b) as compared to peptide, preferably at least 3-fold, at least 5-fold or at least 10-fold more fragmented moiety (b) as compared to peptide. Preferably, these fold-change values apply for optimal energies for compound fragmentation. Preferably, said optimal energies for compound fragmentation are at normalized collision energies (NCE) of 22 or below.

It is furthermore of note that moiety (b) fragments at a single defined site. Fragmentation will give rise to a first and second moiety. While the prior art fails to describe or suggest compounds with the low energy fragmentation and/or high conversion properties of the compound above described, we note that the mentioned first and second moiety have counterparts in reporter moiety and balance moiety of art-established isobaric labeling compounds.

While the first moiety is set free, the second moiety remains bound to the peptide. The molecule or ion consisting of a second moiety and peptide is also referred to as complementary moiety, complementary molecule, complementary ion or peptide-coupled reporter (when used as reporter for quantitation).

The compounds are characterized by high conversion rates while permitting their fragmentation under conditions which leave the attached peptide essentially untouched. The term "conversion" is used herein as being equivalent to fragmentation. Conversions of the compounds are at least 5-fold higher or at least 10-fold higher than that of art-established tandem mass tags (TMT). Preferably, these fold-change values apply for optimal energies for compound fragmentation. Preferably, said optimal energies for compound fragmentation are at normalized collision energies (NCE) of 22 or below.

It is understood that first moiety and second moiety which are formed upon fragmenting of moiety (b) of the compound are not identical. Said moiety (b) does not fragment symmetrically nor is it a symmetrical molecule. Furthermore, when considering the compound as a whole, it is at least preferred that only a single reactive moiety is present. Said single reactive moiety is covalently joined to that part of moiety (b) which is said second moiety. Only thereby it is ensured that, upon fragmenting of the compound in its peptide bound form, a complementary fragment is formed which complementary fragment comprises or preferably consists of the analyte (such as a peptide) and said second moiety.

Furthermore, it is understood that, at least in a preferred embodiment, said compound comprises a single moiety (b).

It is understood that "said energy according to (i)" as recited in item (ii) of the definition of the compound refers to an energy below the threshold for (significant) peptide fragmentation. Furthermore, it is understood that "higher conversion rate" refers to statistically significantly higher conversion rate. Preferably, statistically significantly higher conversion rates occur at normalized collision energies (NCE; see below) up to about 22.

In a preferred embodiment, (a) the energy at which said compound, when coupled to a peptide via said reactive group, fragments with a median conversion rate of about 35%, about 55%, about 75% or about 90% at normalized HCD collision energies of about 17, about 19, about 21 or about 23, respectively; and/or (b) fragmentation at sites other than said single site is below 20%, preferably below 10%, at the energy in accordance with (a).

In a further preferred embodiment, (a) the energy at which said compound, when coupled to a peptide via said reactive group, fragments with a median conversion rate of about 30%, about 45%, about 65%, about 75% or more than 85% at normalized HCD collision energies of about 12, about 14, about 16, about 18 or above 20, respectively.

As noted above, "conversion" and "fragmentation" are used equivalently herein. For example, a conversion rate of 30% means that 30% of the compound get fragmented whereas 70% remain intact. The percentage of compound fragmentation (also called compound conversion) is calculated by dividing the intensity of the peptide-coupled reporter ion (fragmented compound coupled to the non-fragmented peptide) by the summed intensities of the precursor ions (non-fragmented peptide) with intact and fragmented compound.

The abbreviation "HCD" is art-established and refers to high energy collisional dissociation. As a matter of fact, the energy required to fragment a compound depends on the mass and the charge of said compound. In order to have a uniform measure of collision energy (CE), the notion of a normalized collision energy has been introduced. The absolute collision energy can be calculated from the normalized collision energy (NCE) as follows:

$$CE = \frac{NCE}{100} * \left(0.2 - \frac{s}{100}\right) * \frac{m}{s}$$

wherein m is the mass of the compound under consideration, and z is its charge. The NCE is always the same value for each ion, while the absolute collision energy is variable and depends on charge and mass; see, e.g. Neta et al., Journal of the American Society for Mass Spectrometry 20, 469-476 (2009).

Preferably, the above defined normalized collision energies are determined on Q exactive mass spectrometers by Thermo Fisher. On other instruments, analogously normalized energies may be used.

It is apparent from the above that the described compounds are characterized in that they fragment at lower energies than the peptide backbone. One of skill in the art will understand that fragmentation is generally a process which is not characterized by an instantaneous onset when increasing energies. Rather, fragmentation of a molecule which fully fragments at a given NCE may also occur, to a certain degree, at energies which are lower than the given value. For example, significant fragmentation of the peptide backbone occurs at NCE values of 27 and above, but may occur, to a significantly lower degree, also at lower energies. What matters for the purpose of the present invention is that conditions exist where preferential fragmentation of the compound occurs while the backbone of peptides is essentially left intact. A typical NCE value where this applies is an NCE between 5 and 22, preferably between 10 and 22. These are energies where fragmentation of the compound occurs to a statistically significantly higher degree when compared to a fragmentation of the peptide backbone. Accepting the notion of a statistically significant difference between fragmentation rates of the compound on the one hand and the peptide backbone on the other hand, one may introduce the parameter ΔNCE which is defined as follows: NCE at which the peptide backbone fragments to at least 30% minus NCE at which the molecule in accordance with the present invention fragments to at least 30% (see definition of compound fragmentation above, page 8). This value is positive for molecules in accordance with the present invention. It is negative or zero for prior art isobaric tags such as TMT.

The percentage of peptide backbone fragmentation (also called peptide backbone conversion) is calculated by dividing the sum of all fragment ions (b and y ions with intact and fragmented compound) by the summed intensities of peptide fragment ions and peptide precursor ions (summed intensities of b and y and precursor ions with intact and fragmented compound).

In a further preferred embodiment, said compound or said isobaric label comprises one, two, three, four, five, six, seven, eight, nine or ten, or more such as eleven, twelve, thirteen, fourteen, fifteen, sixteen, seventeen, eighteen, nineteen or twenty isotope labeled atoms, isotope labeled atoms preferably being $^{13}$C and/or $^{15}$N.

Isotope labeled mass tags are typically provided in two or more distinct labeled forms, wherein the overall mass is always the same.

While the overall mass is the same, the labeling scheme is chosen in a way which allows variation of the mass of the first moiety and of the second moiety. The maximum number of possible differently labeled compounds having the same overall mass under given labeling scheme defines the maximum degree of multiplexing affordable by the given labeling pattern. To give a simple example, the compound may be designed such that in the first moiety there is exactly one position which may be labeled, and in the second moiety there is also exactly one position which may be labeled. Labeling may be, for example, $^{13}$C labeling. If there is exactly one $^{13}$C label in moiety (b), this may be implemented in two ways, namely either by labeling the mentioned position in the first moiety or by labeling the mentioned position in the second moiety. This yields two isobaric mass tags which are identical in mass, but, upon fragmentation of moiety (b), will yield distinguishable signals.

A higher degree of multiplexing is possible in those instances where first and/or second moiety contain more than one position amenable to labeling.

In structural terms, it is preferred that said compound comprises a moiety of formula (I)

wherein X is SCH$_3$, SO or SO$_2$; Y is CH$_2$, NH or O, provided that (Y)$_n$ comprises 0 or 1 group selected from NH and O; n is 0, 1, 2, 3, 4, 5, 6, 7 or 8, preferably 0 or 1; and Z is CHA-Y or CH$_2$—CO, wherein A is an electron-withdrawing group, preferably NO$_2$ or halogen such as F, wherein preferably said moiety is —SO—(CH$_2$)$_2$—CO—. Also preferred is that said moiety is —SO$_2$—(CH$_2$)$_2$—CO—.

Given that said compound comprises a moiety of formula (I), it is understood that in the (complete) compound, the free valences on X and Z are filled.

Within said formula (I) the bond between (X) and the adjacent CH$_2$ group is the single site as mentioned above at which fragmenting occurs. Importantly, said bond is not a peptide bond. Prior art isobaric tags frequently use a peptide bond as fragmenting site. For that reason, prior art isobaric tags do not provide for selective fragmentation of the tag while leaving the analyte intact. Deviant therefrom, the present compounds are more amenable to fragmentation than peptide bonds. On the other hand, the bond in the compound which is to be fragmented shall not be too fragile either. To explain further, in case of very fragile bonds, a fragmentation would already occur during the process of ionization which is not desirable. As such, the compounds strike a balance between recognizing the advantages of using tags which fragment at lower energies than analytes, especially peptides, on the one hand and the avoidance of relevant fragmentation already in the ionization phase. Relevant fragmentation would be considered to occur if more than 5% of compounds of the invention would fragment during the ionization phase.

Those parts which are not depicted in Formula (I), fragment at higher energies than the X—CH$_2$ bond in formula (I).

Particularly preferred is that X is SO. Particularly preferred is also that X is SO$_2$.

Particularly preferred is that Y is CH$_2$.

Particularly preferred is that n is 0.

Particularly preferred is that Z is CH$_2$—CO.

X does not define a symmetry center of a compound of the invention.

The atoms in formula (I), preferably C and N atoms, can be isotope labeled.

In a further preferred embodiment, said reactive group is selected from N-hydroxy succinimide (NHS); azides including aryl azides such as phenyl azide and nitrophenyl azide; pentafluorophenyl (PFP) esters; psoralen; diazirines; phosphines; acetamides such as iodoacetamide, bromoacetamide and chloroacetamide; iodoacetic acid; maleimide; thiosulfonates; vinylsulfones; pyridyldithiol; alkynes; imidoesters; aryl halides such as difluoro aryl; hydrazides; alkoxyamines; carbodiimides; isocyanates and glyoxal.

Particularly preferred is NHS.

Further reactive groups are at the skilled person's disposal and can be chosen based on the functional group within a given peptide of interest to be targeted; see, for example, Greg T. Hermanson, Bioconjugate Techniques (ISBN: 978-0-12-382239-0). Functional groups in a peptide which may be targeted comprise the amino groups at the N-terminus and in basic amino acids, the sulfhydryl group of cysteine, the hydroxyl group of serine, threonine and tyroxine and the side chain carboxylates of aspartate and glutamate.

Preferably, said compound has formula (II)

B$^1$-formula(I)—B$^2$-D    (II)

wherein B$^1$ and B$^2$ are moieties amenable to multiplexed isotope labeling, preferably multiplexed isotope labeling, preferably at C atoms; D is a reactive moiety as defined in relation to the first aspect; or a salt or solvate thereof, or, to the extent applicable, a tautomer, enantiomer, diastereomer, racemat or mixture thereof.

It is apparent that reactive moiety D is only linked to B$^2$. At least in a preferred embodiment, B$^1$ does not comprise any reactive moiety.

The notion of multiplexed isotope labeling has been explained herein above. Accordingly, it is understood that either one of moieties B$^1$ and B$^2$ contains at least one atom which is amenable to differential isotope labeling. An example of differential isotope labeling is the presence of $^{13}$C at a given position in one isotope labeled form and $^{12}$C (or, in the alternative, the natural isotope distribution) in the other isotope labeled form.

$^{13}$C is a preferred isotope labeled form of a carbon atom. Alternatively or in addition, nitrogen atoms, to the extent they are present in moieties B$^1$ and B$^2$ may be isotope labeled. A preferred isotope label for nitrogen is $^{15}$N.

In a preferred embodiment, B$^1$ is defined by formula (III a) or (III b)

or wherein E is O—CO, S—CO, O—CS, S—CS, (CH$_2$)$_2$ or NH—CO; Y is as defined in relation to formula (I) or CH(CH$_3$); m is 1, 2 or 3; and p is 1, 2 or 3; K is an enrichment moiety; wherein preferably B$^1$ is CH$_3$—CH$_2$—O—CO—CH$_2$, CH$_3$—CH$_2$—NH—CO—CH$_2$, CH$_3$—CH(CH$_3$)—O—CO—CH$_2$, or CH$_3$—CH(CH$_3$)—NH—CO—CH$_2$; and/or B$^2$ is defined by formula (IV a), (IV b) or (IV c)

(IV a)

(IV b)

(IV c)

wherein $R^1$ is H, $C_1$ to $C_4$ alkyl, or cycloalkyl such as cyclopentyl and cyclohexyl; G is a functional group for connecting, to the extent required, $B^2$ to said reactive group D; q is 1, 2, 3, 4, 5, 6, 7 or 8, preferably 1; wherein preferably $B^2$ is NH—$CH_2$—CO.

Optionally, $B^1$ may comprise an enrichment moiety K. This is shown as formula (III b).

Particularly preferred is that E is O—CO.

Particularly preferred is that m is 1.

Particularly preferred is that p is 1.

As noted above, moiety $B^2$ is connected to a reactive group D, group D in turn being designed for coupling to a functional group in an amino acid of a peptide. Depending on the particular design of said reactive group D, it may be advantageous or necessary that there is a connecting group G which provides for connecting the reactive group D to moiety $B^2$. To give an example, for the reactive group D which is NHS, the functional group for connecting, i.e. group G, is CO. When the hydroxy group of NHS binds to said CO, an active ester is formed; see, e.g. formulae (V) below.

Particularly preferred is that $R^1$ is H.

Particularly preferred is that q is 1.

Particularly preferred is formula (IVa).

The compounds are synthetically accessible via art-established routs; see, e.g. Virreira Winter et al., Nature Methods 15, 527-530 (2018).

In a further preferred embodiment, isotope labels are present in one, more or all of $B^1$, formula (I) and $B^2$.

In a further preferred embodiment, said compound has formula (V a) or (V b):

(Va)

wherein $R^2$ is hydrogen or an electron-withdrawing group such as halogen, $NH_3^+$, $NR^3R^4R^{5+}$, or $NO_2$, wherein $R^3R^4$ and $R^5$ are independently $C_1$ to $C_6$ alkyl or cycloalkyl, $C_2$ to $C_6$ alkenyl or cycloalkenyl or $C_2$ to $C_6$ alkinyl;

J is a moiety amenable to isotope labeling and containing C and optionally N and/or O; preferably substituted or unsubstituted $C_1$ to $C_6$ alkyl or cycloalkyl, substituted or unsubstituted $C_2$ to $C_6$ alkenyl or cycloalkenyl, or substituted or unsubstituted $C_2$ to $C_6$ alkinyl, wherein 1 or 2 carbon atoms may be replaced with heteroatoms selected from O, N, S and P, substituents including OH, halogen, methyl and methoxy; J most preferably being $H_3C$—$(CH_2)_r$—O, $H_3C$—$(CH_2)_r$—NH, $H_3C$—$CH(CH_3)$—O or $H_3C$—$CH(CH_3)$—NH;

n is an integer number between 0 and 19, preferably 1; and r is an integer number between 0 and 20, preferably 1;

(Vb)

wherein

$R^2$ is an electron-withdrawing group such as halogen, $NH_3^+$, $NR^3R^4R^{5+}$, or $NO_2$, wherein $R^3$, $R^4$ and $R^5$ are independently $C_1$ to $C_6$ alkyl or cycloalkyl, $C_2$ to $C_6$ alkenyl or cycloalkenyl or $C_2$ to $C_6$ alkinyl;

r and t independently are integer numbers between 1 and 20.

Consistent with moiety X as defined above being particularly preferably SO or $SO_2$, the SO group in formulae (V a) and (V b) as well as in all formulae below may be replaced with $SO_2$.

Related thereto, the present invention provides compounds of formulae (V a) and (V b), provided that SO is replaced with $SO_2$.

In a particularly preferred embodiment, formula (V a) is implemented by formula (V a1)

(Va1)

wherein r is an integer number between 0 and 20; and wherein s is an integer number between 0 and 19.

In a particularly preferred embodiment, formula (V b) is implemented by formula (V b1)

(Va1)

wherein r and t independently are integer numbers between 1 and 20 and $R^3$, $R^4$ and $R^5$ are as defined above.

Preferred in relation to formula (V a1) is that s=r−1. This allows for equal numbers of C atoms amenable to labeling on either side of the fragmentation site.

In a preferred embodiment, r=2 and s=1 (this applies to the compound of Formula (Va3)) or r=4 and s=3 (compound of Formula (Va2)). Molecules meeting this requirement are shown in formulae (V a2) and (V a3). Numbers indicate the C atoms amenable to labeling on either side of the fragmentation site.

(Va2)

(Va3)

The compound of Formula (Va2) allows for multiplexed labeling, viz. 8-plexing, and the compound of Formula (Va3) allows 6-plexing.

Further preferred molecules implementing formula (V a) are:

(Va4)

(Va5)

(Va6)

Similarly, r=1 with s=0 in formula (Va1) allows for 5-plexing, r=2 with s=1 for 6-plexing, and r=3 with s=2 for 7-plexing.

Preferred in relation to formula (V b) is that r=t. This allows for equal numbers of C atoms amenable to labeling on either side of the fragmentation site. In a preferred embodiment r=t=4.

As noted above, $R^3$, $R^4$ and $R^5$ are independently substituted or unsubstituted $C_1$ to $C_6$ alkyl or cycloalkyl, substituted or unsubstituted $C_2$ to $C_6$ alkenyl or cycloalkenyl, or substituted or unsubstituted $C_2$ to $C_6$ alkinyl. Preferred substituents are OH, halogen, methyl and methoxy. Preferred is $R^3$=$R^4$=$R^5$=methyl. Two of $R^3$, $R^4$ and $R^5$ may be together O or S. The third of $R^3$, $R^4$ and $R^5$ may be O or S. For example, $NR^3R^4R^5$ may be $NO_2$.

A preferred embodiment of formula (V b) is shown below.

(Vb2)

A further preferred compound of formula (V a) is the compound of formula (V a7):

(Va7)

Further particularly preferred compounds of formula (V a) are:

(Va8)

(Va9)

(Va10)

In accordance with those preferred embodiments of the formulae above where X is $SO_2$, the following compounds are especially preferred:

(Va11)

(Va12)

Related thereto, the present invention provides an isobaric label of formula (V a11); and an isobaric label of formula (V a12). Also provided is the use of a compound of formula (V a11) or (V a12) as isobaric label.

Coupling of the NHS-containing compound of formula (Va) to a peptide, said peptide bearing an amino group $NH_2$ is illustrated in the following scheme for the compound of formula (V a7):

In a further preferred embodiment, said first moiety is not charged. In other words, upon cleavage of the compound-peptide conjugates to yield first and second moieties, a neutral loss occurs and the charge which originally was present on said conjugate remains in its entirety on the second moiety which is the fragment which comprises the analyte. As a consequence, the m/z of the ions comprising the analytes remains unchanged upon fragmentation. This is advantageous, because the ions of the analyte will appear in a part of the spectrum (lower m/z range) which is generally characterized by high resolution and/or high accuracy. In particular, sensitivity is increased as compared to the prior art because a higher charge state is maintained upon fragmentation.

Further Preferred Embodiments and Further Aspects

Related to the first aspect, the present invention provides in a second aspect a method of analysis using a mass spectrometer, said method comprising collecting precursor ions originating from different analytes in a data-independent manner, wherein said precursor ions carry an isobaric label as defined in accordance with the first aspect.

Throughout this disclosure, preferred isobaric labels are those of formula (II) herein above, noting that reactive moiety D is no longer present when an analyte-label conjugate has been formed.

In a preferred embodiment of the first and the second aspect, all precursor ions occurring in one or more m/z range(s) are collected.

Preferred is that all precursor ions occurring in one m/z range are collected. To the extent more than one m/z ranges are to be used, these are typically ten, twenty, thirty, forty, fifty, sixty, seventy, eighty, ninety, one hundred, two hundred, three hundred or more m/z ranges. Owing to the advantageous properties of the compounds and isobaric labels as described herein above, there are no particular limitations on the choice of the size of the m/z window. In particular, it is not required that the m/z window be tailored to a single peak or a single chemical species. To the contrary, a plurality of peaks or peak clusters corresponding to a plurality of analytes may be comprised in the one or the more m/z ranges in accordance with this preferred embodiment. Typical widths of m/z ranges are fifty, forty, thirty, twenty five, twenty, twelve, ten, nine, eight, seven, six, five, four, three, two and one.

The term "collecting" as used in this disclosure refers to a step of pooling and optionally storing one or more ions within the mass spectrometer, typically prior to—optionally fragmenting and—subjecting them to analysis in the analyzer (or detector). Preferred means of collecting are disclosed further below.

It is understood that the step of collecting includes a step of isolating one or more precursor ions, typically one precursor ion in case of DDA and a plurality thereof in case of DIA. In case of DIA, the precursors are not specifically isolated but isolated together because they are in a certain m/z range that is isolated as a whole. Said isolating is preferably performed with a quadrupole. Accordingly, preferred mass spectrometers are those equipped with a quadrupole.

In a third aspect, the present invention provides use of an isobaric label as defined in relation to the first aspect in mass spectrometry analysis using data-dependent acquisition (DDA).

Related thereto, the present invention provides, in fourth aspect, a method of analysis using a mass spectrometer, said method comprising collecting precursor ions originating from different analytes in a data-dependent manner, wherein said precursor ions carry an isobaric label as defined in relation to the first aspect.

The terms "data-dependent" and "data-dependent acquisition" (abbreviated "DDA") have their art-established meaning (Hu et al. 2016, doi: 10.12688/f1000research.7042.1.). As such, in accordance with a preferred embodiment of third and fourth aspect, precursor ions are collected based on (a) their intensities; and/or (b) prior knowledge.

In other words, the intensities of said precursor ions may be the data which drive the selection of the ions to be selected. Generally, abundant peaks are selected. As a consequence, the selections to be made for the purpose of collecting in the context of data-depending acquisition depend generally on the composition of the sample or the samples to be analyzed. This does not apply, at least generally speaking, to data-independent acquisition.

In the above disclosed alternative (b), selection and collection is based on prior knowledge. Prior knowledge is not particularly limited. It includes instances m/z values and retention times of precursor ions are known from experience in the field of the analysis of related samples or from databases. For example, if a series of samples is to be tested for the presence of a certain peptide, prior knowledge of the location of the peak of said peptide in the mass spectrum in a time and m/z resolution may be employed for the purpose of data-dependent acquisition. In such a case, the m/z range is thus very small like in normal DDA. All other peaks, even though they may be highly intense, are not selected. This is often performed in routine application, e.g. to analyze clinical samples, where large amounts of very similar samples are measured and only few peptides are selected for MS2 analysis.

Preferred analytes are peptides.

In a fifth aspect, the present invention provides a method of operating a mass spectrometer comprising a detector, said detector preferably being an Orbitrap detector or a TOF detector, said method comprising, in the time elapsing during the analysis of fragment ions in said detector, fragmenting of one or more further precursor ions.

Under certain circumstances, the time for analyzing in the detector of fragment ions obtained by fragmentation from precursor ions exceeds the time required for collecting and fragmenting subsequent precursor ions. As a consequence, when using state-of-the-art configuration of the spectrometer, the devices comprised in said spectrometer which are for isolation and fragmentation of precursors are idle while the detector is busy. For Q Exactive instruments with an Orbitrap analyzer, $10^5$ to $5 \times 10^5$ ions are usually collected to obtain an MS2 scan that contains sufficient ions for the identification of the peptide. In Q Exactive instruments, precursor ions are collected and fragmented while the Orbitrap analyzes the m/z of the previous fragmentation scan. While the time to analyze the m/z of the fragment ions in the Orbitrap depends on the desired resolution, the time required for collecting and fragmenting enough precursor ions, depends on the abundance of the precursor ion. Therefore, typically enough precursor ions can be collected for high abundant precursors while the Orbitrap is still busy with analyzing the previous scan.

The higher the resolution of the MS2 scan, the higher the mass accuracy and the better the identification and quantification (since peaks with little mass difference can be resolved and then discriminated from each other). The higher the number of precursors analyzed together in one MS2 scan, the higher the number of identified and quantified peptides sequences in complex peptide mixtures.

Figure 1:
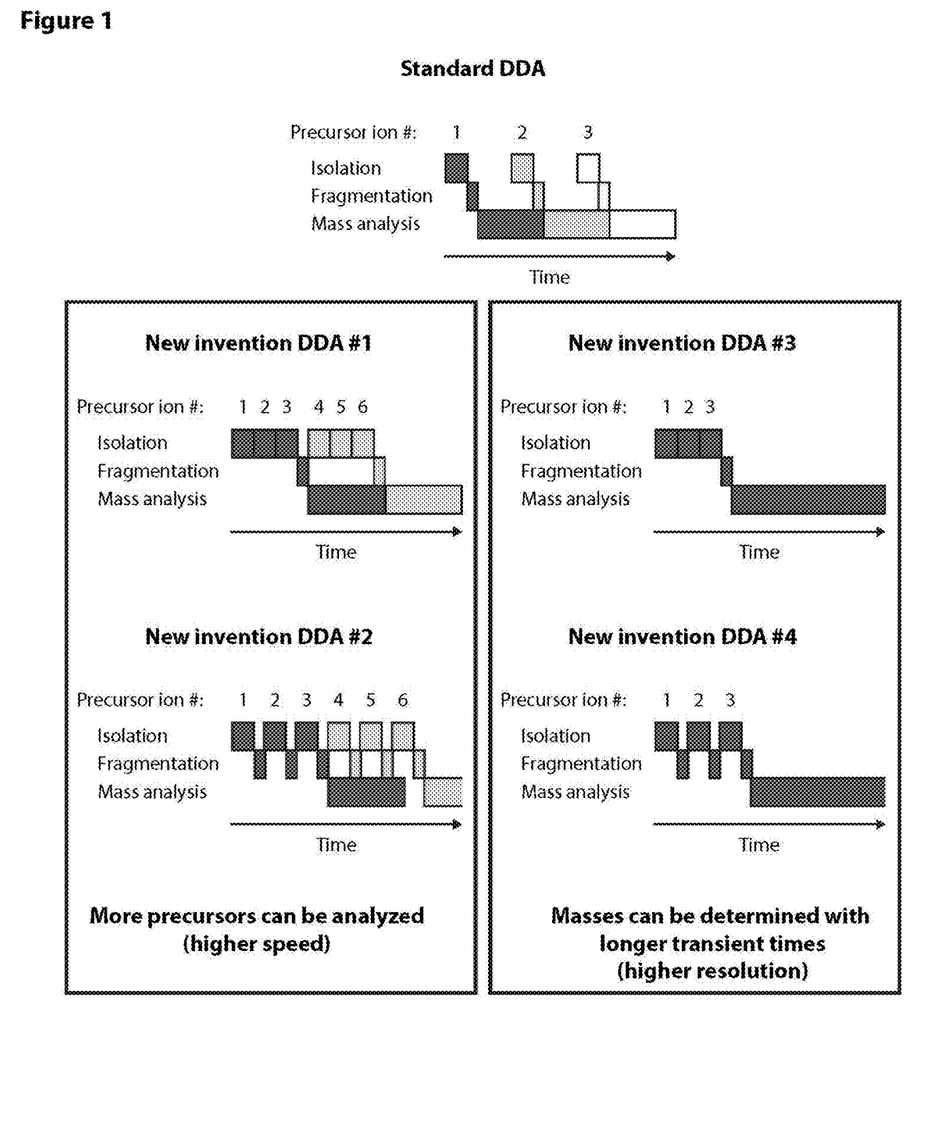
FIG. 1: Mass spectrometer DDA duty cycle schemes in accordance with the invention.

The above aspect advantageously makes use of the mentioned idle time (sufficient ions collected and fragmented but detector still busy). Using state-of-the-art configuration, this idle time is not used to isolate and fragment further ions. In the present invention, the idle time is used to isolate and fragment a second, and, if time permits, third, fourth etc. precursor ion. Thereby, multiple precursor ions may be read out in the same MS2 (fragmentation) scan. By collecting a plurality of precursors, MS2 scans can be performed at higher resolutions. Alternatively, by collecting a plurality of precursors, more precursors can be analyzed at the same resolution without extending the analysis time. This is illustrated in FIG. 1.

To give an example of performing MS2 scans with more precursors at the same resolution: In a standard method on a Q Exactive HF Orbitrap instrument $10^5$ precursor ions are collected within 55 ms, then fragmented and analyzed with a resolution of 30,000 at m/z 200, resulting in a transient time of 64 ms. Using the method of the invention, e.g. 2 different precursor ions ($10^5$ ions each) are collected within 55 ms (e.g. 25 ms is enough to collect $10^5$ ions of each precursor) and subsequently fragmented and analyzed with a resolution of 30,000 at m/z 200, resulting in a transient time of 64 ms.

To give an example of performing MS2 scans at higher resolution:

In a standard method on a Q Exactive HF Orbitrap instrument $10^5$ precursor ions are collected within 55 ms, then fragmented and analyzed with a resolution of 30,000 at m/z 200, resulting in a transient time of 64 ms. Using the method of the invention, e.g. 2 different precursor ions ($10^5$ ions each) are collected within 110 ms (55 ms is enough to collect $10^5$ ions of each precursor) and subsequently fragmented and analyzed with a resolution of 60,000 at m/z 200, resulting in a transient time of 128 ms. In that case, the two precursors are analyzed with a higher resolution within the same time frame.

In a preferred embodiment of the method of the fifth aspect, during said time, and prior to said fragmenting, said one or more further precursor ions are collected.

In a further preferred embodiment, more further precursor ions such as two, three, four, five, six, seven, eight, nine, ten, 20, 50 or 100 further precursor ions are collected and fragmented.

It is understood that the notion of "further" precursor ions is meant to distinguish between precursor ions which have already been fragmented and are now analyzed in a detector on the one hand and those precursor ions which are collected and fragmented in the meantime. The latter are referred to as "further precursor ions" in context of the fifth aspect of the invention.

Figure 2:
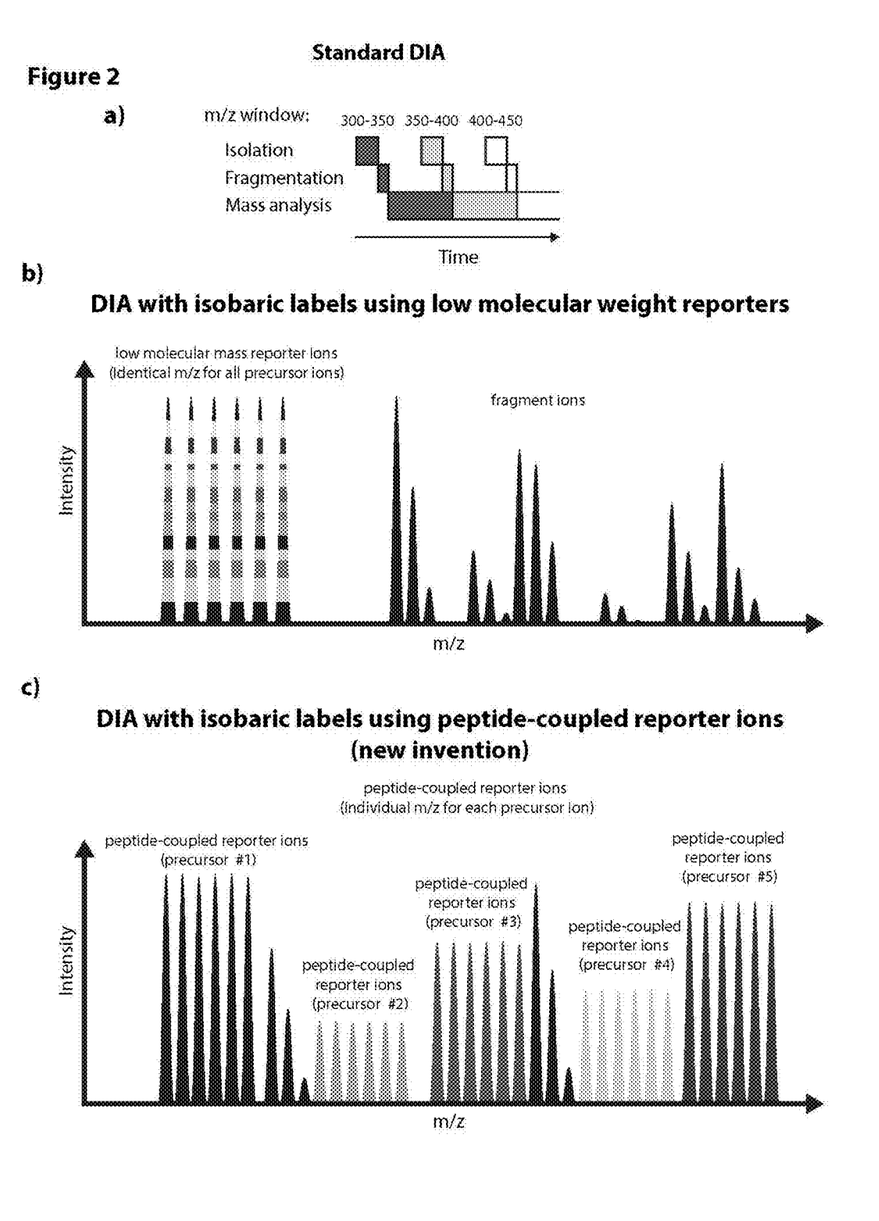
FIG. 2: Data-independent acquisition (DIA) with isobaric labels

The method of the fifth aspect is preferably combined with the methods of second and fourth aspect. As such, provided is a method of analysis using a mass spectrometer, said method comprising collecting precursor ions originating from different analytes in a data-independent manner, wherein said precursor ions carry an isobaric label as defined above, said method further comprising, in the time elapsing during the analysis of fragment ions in the detector of said mass spectrometer, collecting and fragmenting of one or more further precursor ions (FIG. 2). Also provided is a method of analysis using a mass spectrometer, said method comprising collecting precursor ions originating from different analytes in a data-dependent manner, wherein said precursor ions carry an isobaric label as defined above, said method further comprising, in the time elapsing during the analysis of fragment ions in the detector of said mass spectrometer, fragmenting of one or more further precursor ions.

In a preferred embodiment, said precursor ions carry an isobaric label, preferably an isobaric label as defined herein above.

In a further preferred embodiment, said fragment ions which are analyzed in said detector originate from a plurality of precursor ions.

In accordance with this preferred embodiment, not only a plurality of precursor ions may be collected and fragmented, but furthermore a plurality of precursor ions has given rise to those fragment ions which are being analyzed in the detector.

Altogether, it is particularly preferred that in subsequent duty cycles of the mass spectrometer always a plurality of precursor ions is collected and fragmented, while at the same time fragment ions originating from a plurality of precursor ions are analyzed; see also FIG. 1.

In a further preferred embodiment, the time allocated for analyzing is increased, with the number of precursor ions in said plurality.

This preferred embodiment illustrates a particularly preferred feature of the invention, namely the improved use of time on the spectrometer. To explain further: the isobaric tags (herein also referred to as "compounds") as disclosed herein above permit the pooling ("collecting") of precursor ions originating from distinct analytes. As a consequence, more ions are analyzed within a given time. The time allocated and spent by the detector for analyzing within one duty cycle of the mass spectrometer is also referred to as "transient time". If in the conventional approach (using art-established isobaric labels) N duty cycles are necessary for analyzing N analytes. This can be reduced to a single duty cycle when using the above disclosed isobaric labels. This single duty cycle can be up to N times longer than the standard duty cycle of the mass spectrometer. Accuracy and resolution of the mass spectrum benefit significantly therefrom.

The above scheme may also be adjusted dynamically, for example, in dependency of the ion current. High abundant precursor ions require less time for collecting a sufficient number of ions, typically between $0.5 \times 10^5$ and $5 \times 10^5$, than low abundant precursor ions. Therefore, if there are multiple high abundant precursor ions detected in the full (MS1) scan, more precursor ions can be collected in the same time frame.

The increase of the transient time can be up to N times.

In those instances where the above disclosed increase of transient time is not necessary or desirable, the pooling of precursor ions may be used for enhancing throughput. These two alternatives (enhancement of resolution and enhancement of throughput) are illustrated in FIG. 1. They may also be combined.

In a further preferred embodiment, said method is a data-independent acquisition (DIA) method or a data-dependent acquisition (DDA) method.

The concepts of data-independent and data-dependent acquisition are discussed herein above.

In a further preferred embodiment, said isobaric label (a) is as defined in relation to the first aspect of the present invention; (b) is selected from isobaric labels such as TMT and iTRAQ which isobaric labels fragment at or above energies required for fragmenting analytes which are peptides. These (generally art-established) labels work to the extent one further precursor ion is fragmented in said time, in particular for the purpose of analyte quantitation.

The above option (b) makes use of art-established isobaric labels. As mentioned above, these are characterized in that they do not preferentially fragment at energies which are significantly lower than the energies required for fragmenting the peptide backbone. When using these art-established isobaric labels for quantitation, one has to rely on reporter fragments which do not carry any structural analyte signature (low molecular mass reporters). Therefore, and in order to maintain quantitative information, only one further precursor ion may be fragmented while the detector is busy and subsequently only fragment ions originating from one precursor ion species may be analyzed.

In a preferred embodiment of all aspects of the present invention directed to methods, said method comprises at least one non-fragmenting scan (MS1) and at least one fragmenting scan (MS2), wherein said non-fragmenting scan yields the precursor ions to be fragmented in said at least one fragmenting scan.

In a further preferred embodiment, (a) collecting is performed in an ion trap, preferably a C-trap; (b) fragmenting of the precursor ions is sequential or all precursor ions are fragmented together; and/or (c) fragmenting is performed in a collision cell.

Taken together, preferred mass spectrometers for performing methods and uses of the present invention are equipped with a device for isolating precursor ions, preferably a quadrupole; a device for fragmenting precursor ions and/or isobaric labels, preferably a collision cell; and a mass analyzer or detector which serves to determine m/z values. A preferred detector is an Orbitrap detector, especially in conjunction with the method of the fifth aspect. Otherwise, time-of-flight (TOF) detectors may be used. Preferably, and typically in conjunction with an instrument comprising an Orbitrap detector, the mass spectrometer comprises a device for collecting precursor ions, preferably a C-trap.

As noted above, the plurality of precursor ions to be fragmented may be fragmented together. In the alternative, they may be fragmented sequentially. This is of interest in case different precursor ions have very different fragmentation behavior, especially if fragmentation occurs at different energies. In such a case, each precursor is treated with those collision energies which provide for sufficient conversion. The two approaches may also be combined, for example, a large number of precursors may be partitioned in two or more groups, wherein the members of each group share the property that they fragment with similar conversion rates at similar energies. Required collision energies would vary significantly between groups.

The sequential option (separate fragmentation of each isolated precursor) is illustrated in FIG. 1 as is the parallel fragmentation of a plurality of precursors together.

In an alternative, a trapped ion mobility spectrometry-time of flight (timsTOF) instrument, preferably equipped with parallel/serial fragmentation (PASEF) may be used; see, e.g. Meier et al. 2015, doi: 10.1021/acs.jproteome.5b00932. This is preferred for the method of the first aspect.

In a further preferred embodiment, said fragmenting comprises one or both of (i) fragmenting the conjugates of precursors and said group at an energy where said conjugates preferentially fragment at said single site within said group, thereby giving rise to precursor-coupled reporter ions; and (ii) fragmenting said conjugates of precursors and said group at an energy that fragments both said group and said precursors; wherein, to the extent (i) and (ii) are both performed, they are performed concomitantly or subsequently in any order.

Both of fragmenting in accordance with (i) and fragmenting in accordance with (ii) may be referred to as "MS2 scan". Preferred is performing both (i) and (ii).

Preferably, said precursor ions are or comprise peptide ions. In that case, the above recited precursor-coupled reporter ions are in fact peptide-coupled reporter ions.

In terms of nomenclature, and in view of the above option (ii) it is noted that the term "peptide-coupled reporter ion" preferably embraces a set of distinct species. These species share that they comprise a fragment of the isobaric label. They furthermore share that they comprise a peptide. Having said that it is noted that the peptide component may differ within said set of species. While there is a species which comprises the entire and unfragmented peptide, there are also species (usually a plurality) where the peptide has been fragmented as well and only that fragment of the original peptide analyte is comprised in the peptide-coupled reporter ion which is directly adjacent to the label. This is advantageous and accuracy and precision of quantitation increases with the number of distinct species within a given set of peptide-coupled report ions. The species within one set share that they originate from the same peptide precursor.

In a further preferred embodiment, exact masses of peptide-coupled reporter ions are determined. To explain further, high resolution MS2 scans are required to resolve and quantify the peptide-coupled fragment ions if the mass difference between the differently isotope labeled isobaric labels is less than 1 Da, for example when the tags are neutron-encoded. In isobaric labeling, the tags usually are distinguished by incorporation of a different number of heavy carbon atoms. Therefore, the mass difference between molecules is about 1 Da. To increase the multiplexing capacity, also other atoms in the molecule can be substituted by heavier isotopes of these atoms (e.g. nitrogen, but also others). In that case, the mass difference between a light and heavy nitrogen must be distinguished from the mass difference between a light and heavy carbon. This mass difference is only about 6 mDa. Therefore, a much higher resolution is required.

As explained herein above, collecting a plurality of precursor ions, fragmenting them (sequentially or together), and analyzing them together allows to significantly extend transient times. Extended transient times in turn enable the determination of exact mass differences. This is made possible by the isobaric labels as defined in relation to the first aspect. In those instances where the reporter ions do not comprise any structural signature of the analyte (i.e., no fragment thereof), there is no possibility to assign the determined reporter intensities to a specific precursor. For that reason, in case of the analysis of reporter ions which are not analyte-coupled reporters, only a single precursor ion can be analyzed in each instance.

As such, the isobaric labels as defined in conjunction with the first aspect provide for an important lead forward, especially in the field of data-independent acquisition. Also, it should be noted that the longer transient times do not compromise the overall acquisition speed, because the isobaric labels disclosed herein above allow for the collecting of a plurality of precursors.

In a further preferred embodiment of any of the aspects of the present invention directed to methods, said method comprises separating analytes which give rise to said precursors, preferably by chromatography such as liquid chromatography (LC), wherein preferably said chromatography is coupled online to said mass spectrometer (online LC-MS).

In a particularly preferred embodiment, a plurality of samples is pooled prior to said chromatography, wherein analytes in different samples carry isobaric labels with different isotope substitution.

This preferred embodiment implements the combination of isobaric labeling and sample pooling as mentioned in the introductory section. Sample pooling and isobaric labeling is art-established; what is distinguishing the present invention therefrom is the new type of isobaric label disclosed herein above as well as in WO 2018/087397. The use of isobaric labels as disclosed in conjunction with the first aspect provides for a double increase of throughput: first, the pooling of samples is made possible by isobaric labeling, and the specific isobaric labels disclosed herein provide for the pooling ("collecting") of precursors originating from different analytes prior to fragmenting and analyzing.

Accordingly, provided is a method of analysis using a mass spectrometer, said method comprising: (a) pooling samples, wherein analytes in different samples carry isobaric labels as defined above, with different isotope substitution; (b) separating said analytes by chromatography; (c) performing a non-fragmenting scan in the mass spectrometer; (d) collecting precursor ions originating from different analytes in a data-independent manner; (e) performing fragmenting, wherein said fragmenting comprises (i) fragmenting the conjugates of precursors and said label at an energy where said conjugates preferentially fragment at said single site within said label, thereby giving rise to precursor-coupled reporter ions; and (ii) fragmenting said conjugates of precursors and said label at an energy that fragments both said label and said precursors.

Also provided is an analogous method for DDA.

In a further preferred embodiment, the method comprises collecting same precursor ions more than once, thereby obtaining a plurality of data points for a given peak in said chromatography. This applies in particular in conjunction with DDA.

This increases confidence in identification and quantitation by mass spectrometry. An associated computer-implemented method for MS data analysis is also subject of the present invention; see further below.

In case of overlapping peaks in the chromatogram (partial overlap of different analytes), this gain in confidence is particularly valuable.

Confidence is further increased when, in accordance with the preferred embodiment disclosed further above, not only a non-fragmenting scan, but furthermore at least one fragmenting scan are performed. In that case, one can determine by means of correlation analysis which fragment ions correspond to which precursor ions. This in turn allows analyte identification at a high level of confidence. This is preferred in conjunction with DIA.

The correlation of precursor ion elution profiles with fragment ion elution profiles is particularly useful when data-independent acquisition is performed. The term "elution profile" is associated with the mentioned peak in the chromatogram. More specifically, a single peak in the chromatogram gives rise to two elution profiles, one elution profile being associated with the precursor ions originating from the analyte giving rise to the peak, and a second elution profile being associated with the fragment ions obtained from said precursor ions in the course of an MS2 scan.

In a further preferred embodiment, individual steps of said collecting more than once are separated by (a) given time interval(s) such as an interval of one, two, three, four or five seconds between subsequent steps of collecting.

In a particularly preferred embodiment, elution profiles of precursor ions are correlated with elution profiles or fragment ions.

In a sixth aspect, the present invention provides a computer-implemented method of analysing MS data, said method comprising calculating of m/z values of analytes, said calculating making use of observed m/z values of a plurality of analyte-coupled reporter ions, the analyte moieties in said ions being identical. In a preferred embodiment, the reporter moieties in said ions differing from each other by known m/z differences. The differences are known because structure and isotopic substitution of the isobaric labels are known.

In another preferred embodiment, said reporter moieties originate from isobaric labels as defined in the first aspect.

In a further preferred embodiment of the above disclosed computer implemented method, said data are generated with the above disclosed methods of analysis of a plurality of pooled samples.

Preferably, the analytes in the context of the computer-implemented method are or comprise peptides.

To give an example, if the label breaks, each peptide-derived fragment ion (b- and y-ions) and also the precursor ion with fragmented tag will give rise to an ion cluster, because each channel will have a distinct mass with a difference of about 1 Da between the x channels (e.g. 6 channels). This means that for each fragment ion, there are usually x+1 measured m/z values (with x=number of channels), because there are the x ions from the ion cluster and the same fragment ion with an intact tag. All these measured values can be used to calculate the m/z of the fragment ion with a higher mass accuracy as compared to only one measured m/z value being available (which is the case for any unlabeled fragment ion).

Examples of peptide fragments are b-ions and y-ions. The term "peptide fragment" may also include the unfragmented peptide.

In a further preferred embodiment, accuracy and precision of quantitation is increased by quantifying multiple peptide-coupled reporter ions for each precursor ion.

The amount of a given peptide may be determined as median or mean, or weighted median or mean, of the peak intensities observed for the fragments obtained in (i) and (ii) belonging to or originating from a given precursor ion. To the extent weighted averages are used, higher weights are preferably given to higher peaks, given that those peaks are more precise and accurate. Also, peaks with a signal-to-noise ratio of less than 3 are preferably disregarded. An additional or alternative means of improving processing of MS data obtained with compounds of the invention is the following. Each constant part, i.e. fragment of the compound of the invention attached to the peptide analyte defines a "channel". Each b-ion and each y-ion defines a cluster in the spectrum, and there are clusters in each channel. If a cluster has a different distribution of intensities from all others, the channel that exhibits said different distribution is deleted.

In terms of advantages, we have noted herein above that the compounds of the present invention allow for a significant reduction of interference by co-eluting peptides. The present preferred embodiment is yet an additional means to further reduce interference. The problem of ratio compression (which is well-known in the art) is further mitigated by this preferred embodiment. In particular, averaging improves accuracy and precision. The coefficient of variation is typically reduced by at least 25%. Finally, while in the absence of these measures, MS3 might be necessary, MS2 is sufficient in many instances when performing averaging. MS3 would even not be more accurate. The benefit of the peptide-coupled reporter ions vs. MS3 is that the resolution of m/z determination by an Orbitrap detector is always higher than any quadrupole-based isolation such as MS3.

A plurality of analyte-coupled reporter ions, the analyte moieties in said ions being identical, may also originate, in an alternative, or in combination with the above disclosed preferred embodiment of the sixth aspect, from the multiple sampling of a peak in a chromatography coupled online to the mass spectrometer. In particular, and as disclosed above, a plurality of the data points for a given peak in said chromatography may be obtained. Noting that, in line with common understanding, the term peak in conjunction with chromatography designates the occurrence of a given analyte as a function of time, the same analyte is analyzed in the mass spectrometer multiple times if during the elution of the peak multiple samples are fed into the mass spectrometer.

In a particularly preferred embodiment, the multitude of data points corresponding to a given analyte originates from both multiple samples being drawn from a given peak in the chromatogram and from multiple differently labeled precursor ions. The term "differently labeled" in this context refers to isobaric labels of the same structure, but of different isotope substitution patterns.

In a further aspect, the present invention provides a computer program comprising instructions to cause a computer to execute the steps of the method of any one of the preceding aspects, said computer being comprised in a mass spectrometer.

In a further aspect, the present invention provides a computer-readable medium (a) comprising instructions which, when executed on a computer, cause said computer to execute the steps of the method of any one of the preceding aspects, said computer being comprised in a mass spectrometer; and/or (b) having stored thereon the computer program of the preceding aspect.

In a further aspect, the present invention provides a mass spectrometer comprising a computer, said computer comprising means for carrying out the method of any one of the preceding aspects, such means preferably being the computer program of the present invention and/or the computer-readable medium of the present invention.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show:

FIG. 1: Mass spectrometer DDA duty cycle schemes in accordance with the invention. Standard DDA: Typically, following a Full (MS1) scan, 5-20 precursor ions (shown are only 3 precursors) are sequentially isolated, fragmented and their fragment ion masses are determined in the detector (MS2 scan). Typically, this takes 0.5-3 seconds. The figure only shows the duty cycle schemes for MS2 scans.

DDA #1: Multiple precursor ions (shown are only 6 precursors) are isolated sequentially, fragmented together and their fragment ion masses are determined together. Typically, this takes 0.5-3 seconds. The figure only shows the duty cycle schemes for MS2 scans.

DDA #2: Multiple precursor ions (shown are only 6 precursors) are isolated and fragmented sequentially and their fragment ion masses are determined together. Typically, this takes 0.5-3 seconds. The figure only shows the duty cycle schemes for MS2 scans.

DDA #3: Multiple precursor ions (shown are only 3 precursors) are isolated sequentially, fragmented together and their fragment ion masses are determined together with long transient times to obtain a higher resolution mass analysis. Typically, this takes 0.5-3 seconds. The figure only shows the duty cycle schemes for MS2 scans.

DDA #4: Multiple precursor ions (shown are only 3 precursors) are isolated and fragmented sequentially and their fragment ion masses are determined together with long transient times to obtain a higher resolution mass analysis. Typically, this takes 0.5-3 seconds. The figure only shows the duty cycle schemes for MS2 scans.

FIG. 2: Data-independent acquisition (DIA) with isobaric labels

The examples illustrate the invention.

EXAMPLE 1

DIA with Isobaric Labels

With reference to FIG. 2, exemplary implementations of the first and second aspect of the invention are described.
a) Duty cycle scheme for a standard DIA acquisition. Following a Full (MS1) scan, typically mass windows of 12.5-50 m/z (50 m/z shown here) containing multiple precursor ions are isolated, fragmented and their fragment ion masses are determined together. The windows are sliding over the whole mass range, typically 300 m/z-1650 m/z within a cycle time of about 1-5 seconds (only the windows between 300 m/z and 450 m/z are shown). FIG. 2 only shows the duty cycle schemes for MS2 scans.
b) In a data-independent acquisition scheme, each MS2 scan contains fragment ions of multiple precursor ions. Low molecular mass reporter ions of state-of-the-art isobaric labels (without peptide-specific information) cannot be assigned to individual precursor ions, because they are identical for each precursor ion. Fragment ions (depicted in the higher m/z range) are used to identify precursor ions. Quantification of multiple precursor ions and multiplexed samples within a DIA acquisition scheme is not possible with low molecular mass reporter ions.
c) Peptide-coupled reporter ions can be assigned to individual precursor ions, because they contain peptide-specific information. Peptide-specific reporter ions can be precursor ions with fragmented tag but also fragment ions (b- and y-ions) with fragmented tag. Thereby, simultaneous quantification of multiple precursor ions and multiplexed samples within a DIA acquisition scheme can be achieved. Peptide-coupled reporter ions and fragment ions without tag are used to identify and quantify precursor ions.

The invention claimed is:

1. A method for using an isobaric label in mass spectrometry (MS) analysis using data-independent acquisition (DIA), wherein said isobaric label comprises or consists of a group which fragments in the mass spectrometer, said method comprising:
(i) fragmenting the group at an energy below the energy required for fragmenting analyte-derived precursor ions and/or a higher conversion rate than said precursor ions; and
(ii) fragmenting the group at said energy according to (i) and when coupled to a precursor ion, at a single site within said group, to yield a first moiety and a second moiety, said second moiety being coupled to said precursor ion.

2. The method of claim 1, further comprising using the isobaric label in mass spectrometry analysis using data-dependent acquisition (DDA).

3. The method of claim 1, wherein said method further comprises performing at least one non-fragmenting scan (MS1) and at least one fragmenting scan (MS2), wherein said non-fragmenting scan yields the precursor ions to be fragmented in said at least one fragmenting scan.

4. The method of claim 1, wherein said method further comprises separating analytes which give rise to said precursors, by chromatography comprising liquid chromatography (LC), wherein said chromatography is coupled online to said mass spectrometer (online LC-MS), wherein a plurality of samples is pooled prior to said chromatography, wherein analytes in different samples carry isobaric labels with different isotope substitution.

5. The method of claim 1, wherein said isobaric label comprises the moiety of formula (I)

$$-SO_2-(CH_2)_2-CO-. \quad (I)$$

6. The method of claim 5, wherein said isobaric label has formula (V a11) or (V a12)

7. A method of analysis using a mass spectrometer and data-independent precursor collection, said method comprising:
collecting precursor ions originating from different analytes, wherein said precursor ions carry an isobaric label, wherein said isobaric label comprises or consists of a group which fragments in the mass spectrometer, said method further comprising:
(i) fragmenting the group at an energy below the energy required for fragmenting analyte-derived precursor ions and/or a higher conversion rate than said precursor ions; and
(ii) fragmenting the group at said energy according to (i) and when coupled to a precursor ion, at a single site within said group, to yield a first moiety and a second moiety, said second moiety being coupled to said precursor ion.

8. A method of analysis using a mass spectrometer and data dependent precursor collection, said method comprising:
collecting precursor ions originating from different analytes, wherein said precursor ions carry an isobaric label, wherein said isobaric label comprises or consists of a group which fragments in the mass spectrometer, said method further comprising:

(i) fragmenting the group at an energy below the energy required for fragmenting analyte-derived precursor ions and/or a higher conversion rate than said precursor ions; and (ii) fragmenting the group at said energy according to (i) and when coupled to a precursor ion, at a single site within said group, to yield a first moiety and a second moiety, said second moiety being coupled to said precursor ion.

\* \* \* \* \*